(12) United States Patent
Rutherford et al.

(10) Patent No.: US 6,726,903 B2
(45) Date of Patent: Apr. 27, 2004

(54) MONO AND DIALKYL QUATS IN HAIR CONDITIONING FOAMING COMPOSITIONS

(75) Inventors: Keith Leslie Rutherford, Palatine, IL (US); Mrunalini Shireesh Dhamdhere, Des Plaines, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 1 day.

(21) Appl. No.: 10/188,634

(22) Filed: Jul. 3, 2002

(65) Prior Publication Data

US 2004/0005287 A1 Jan. 8, 2004

(51) Int. Cl.$^7$ ............................................... A61K 7/075
(52) U.S. Cl. ...................... 424/70.27; 424/45; 424/701
(58) Field of Search .............................. 424/701, 70.27, 424/45

(56) References Cited

U.S. PATENT DOCUMENTS

| | | | |
|---|---|---|---|
| 4,818,523 A | | 4/1989 | Clarke et al. |
| 4,859,456 A | * | 8/1989 | Marschner .................. 424/47 |
| 4,976,956 A | | 12/1990 | Noe |
| 6,613,316 B2 | | 9/2003 | Sun et al. |
| 2002/0015686 A1 | | 2/2002 | Pyles |
| 2002/0106343 A1 | | 8/2002 | Sun et al. |

FOREIGN PATENT DOCUMENTS

| WO | 00/07562 | 2/2000 |
|---|---|---|
| WO | 00/48556 | 8/2000 |

OTHER PUBLICATIONS

JP 56169617 assigned to Lion Corp (Derwent Abstract only), Dec. 1981.
JP 56169615 assigned to Lion Corp (Derwent Abstract only), Dec. 1981.
JP 56169614 assigned to Lion Corp (Derwent Abstract only), Dec. 1981.
JP 56169613 assigned to Lion Corp (Derwent Abstract only), Dec. 1981.
JP 87008086 assigned to Lion Corp (Derwent Abstract only), Dec. 1981.
JP 87008087 assigned to Lion Corp (Derwent Abstract only), Dec. 1981.
JP 87008088 assigned to Lion Corp (Derwent Abstract only), Dec. 1981.

* cited by examiner

*Primary Examiner*—Jyothsna Venkat
(74) *Attorney, Agent, or Firm*—Milton L. Honig

(57) ABSTRACT

The present invention relates to a foaming hair conditioner which comprises a monoalkyl quat from C14 to higher carbon chain lengths (preferably C16 to C22) and a dialkyl quat which is a mixture of C16, C16 dialkyl quat and C18, C18 dialkyl quat. Optionally, a silicone compound may be included. The monoalkyl quat may be in a ratio to the dialkyl quat of about 15:1 to about 2:1. The carbon chain lengths within the dialkyl quat are present in a weight ratio of about 1:3 to about 3:1 of C16, C16 dialkyl quat to C18, C18 dialkyl quat.

19 Claims, No Drawings

MONO AND DIALKYL QUATS IN HAIR CONDITIONING FOAMING COMPOSITIONS

BACKGROUND OF THE INVENTION

Most individuals buy and use a hair shampoo for its cleansing properties. In addition to having clean hair, a consumer also desires sufficiently-conditioned hair that holds a preset configuration. However, hair shampoos generally are formulated with highly effective anionic surfactants that primarily clean as opposed to conditioning the hair. Anionic surfactants not only remove the dirt and soil from the hair, but also remove lipids naturally present on the surface of the hair fibers. Therefore, the desirable cleansing properties of anionic surfactants also leave the hair in a cosmetically-unsatisfactory condition. Shampoos also do not help to detangle wet hair and do not impart residual conditioning benefits to dry hair, such as manageability or styleability of hair sets.

In general, shampoo compositions containing anionic surfactants, or nonionic surfactants or amphoteric surfactants, leave the hair with an undesirable harsh, dull and dry touch, or feel, usually called "creak", after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing property of dry hair remains poor, and the hair has undesirable electrostatic properties in a low humidity atmosphere that causes the hair to "fly away", thereby further reducing the brushing properties of the hair.

The unsatisfactory combing or brushing property of hair immediately after shampooing, or during trimming treatments after shampooing, also causes hair damage, such as split ends or hair breakage. In addition, the natural luster and resiliency of the hair is reduced. The overall unsatisfactory condition of shampooed hair often necessitates a subsequent post-shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. The wet combing problem has been solved by treating shampooed hair with a conditioner composition that coats the hair shaft and causes the individual hair shafts in a tress to resist tangling and matting because of the smooth coating provided by conditioner molecules on the shaft.

However, the need for improved compositions that condition the hair, i.e., render the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair often are used to complete the hair cleansing and hair conditioning cycle.

The ability of cationic compounds to adsorb to or interact with the keratinous material of the hair makes these compounds desirable for improving wet hair detangling and dry hair manageability. However, cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought.

The following is a list of patents and patent applications in this field.

U.S. Pat. No. 4,818,523 discloses a stable easily removable hair rinse conditioner which provides good conditioning, styling ease, and manageability of hair, but does not build up and is cost effective, consisting essentially of effective amounts of a dodecyl trimethyl quaternary ammonium compound, a saturated or unsaturated $C_{14}$–$C_{22}$ alkanol, and a cyclic or linear silicone, in an aqueous vehicle.

U.S. Pat. No. 4,976,956 discloses a method of imparting improved conditioning properties to hair comprising treating the hair with a composition comprising a water-soluble quaternary ammonium compound, such as cetrimonium chloride; an oil-soluble, water-dispersible quaternary ammonium compound, such as distearyldimonium chloride; an acid-neutralized amidoamine compound, and a low molecular weight polydimethylsiloxane compound, such as cyclomethicone. The method and composition unexpectedly provide improved hair-conditioning properties such as wet feel, wet and dry combing, manageability, sheen, luster, body and overall hair condition.

WO 00/07562 discloses hair conditioning compositions comprising silicones and mono and dialkyl quats.

WO 00/48556 discloses hair conditioning compositions comprising silicones and mono and dialkyl quats.

U.S. Pat. 6,613,316 (Sun et al.) discloses an aqueous opaque hair conditioner which comprises a monoalkyl quat from C14 to higher carbon chain lengths (preferably C16 to C22) and a dialkyl quat which is a mixture of C16, C16 dialkyl quat and C18, C18 dialkyl quat. Also included is an amount of fatty alcohol to opacify the conditioner. Optionally, a silicone compound may be included. The monoalkyl quat may be in a ratio to the dialkyl quat of about 15:1 to about 2:1. The carbon chain lengths within the dialkyl quat are present in a weight ratio of about 1:3 to about 3:1 of C16, C16 to C18, C18. The fatty alcohol may be present in an amount from about 1% to about 10%.

There are a series of patents from Lion Corp that describe the use of a monoalkyl and a dialky quat mixture in a conditioner. These are Japanese Patents JP 56169617 A, JP 56169615 A, JP 87008088, JP 56169614 A, JP 87008087 B, JP 56169613 A, JP 87008086 B and U.S. Pat. No. 4,976,956.

The present invention is directed to a foaming conditioning composition that is esthetically acceptable to consumers, improves the wet combing and dry combing properties of hair, and also leaves the dry hair with satisfactory cosmetic and physical properties, including, in particular, dry combing and feel, less hair coating, manageability, body, condition of the ends and set.

SUMMARY OF THE INVENTION

The invention is a foaming conditioner that has a combination of two different types of conditioning agents, an emulsifier, and a blend of propellants.

The purpose of the invention is to provide a foaming hair conditioner with improved performance, while using effective materials at ratios that optimize their benefit.

The present invention relates to a foaming hair conditioner which comprises a monoalkyl quat from C14 to higher carbon chain lengths (preferably C16 to C22) and a dialkyl quat selected from a mixture of C16, C16 dialkyl quat and C18, C18 dialkyl quat.

The present invention relates to a foaming hair conditioning composition comprising:
(a) a monoalkyl quat having 14 or greater carbon atoms in an alkyl substituent; preferably the monoalkyl quat has 16 to 22 carbon atoms.
(b) and a dialkyl quat selected from a mixture of C16,C16 dialkyl quat and C18,C18 dialkyl quat;
(c) optionally a silicone compound; and
(d) a propellant.

Another aspect of the invention is to provide a method of treating the hair to yield well-conditioned hair having esthetically pleasing physical properties by contacting the hair with a foaming conditioner of the present invention.

DETAILED DESCRIPTION OF THE INVENTION

Unless indicated otherwise, as used herein, "%" means weight %. The starting materials set forth herein are either known or can be prepared in accordance with known methods. As used herein, "C16, C16 dialkyl quat" or "C16 dialkyl quat" or "(Di-$C_{16}$) quat" refers to a quaternary ammonium compound wherein two of the alkyl substituents are the same and each of these alkyl substituents contains 16 carbon atoms. As used herein, "C18, C18 dialkyl quat" or "C18 dialkyl quat" or "(Di-$C_{18}$) quat" refers to a quaternary ammonium compound wherein two of the alkyl substituents are the same and each of these alkyl substituents contains 18 carbon atoms. As used herein, ratio means weight ratio.

The current invention teaches a new and improved conditioning formulation based on cationic compounds in which enhanced wet and dry hair properties can be achieved. The technology relates to a foaming formulation that provides substantial conditioning benefit without compromising the styling attributes to consumers.

Recently, it has been found that a mixture of monoalkyl quat and dialkyl quat of specific chain length can provide superior conditioning benefit compared to that provided by either monoalkyl or dialkyl quat alone. However, the wet and dry stage performance is still not comparable to the silicone oil-containing conditioners. This invention teaches a mixed monoalkyl quat (preferably C16 to C22) and dialkyl quat system in which the dialkyl quat contains mixtures of specific hydrocarbon chain lengths (preferably C16 to C18). It has been found that an enhanced wet and dry stage conditioning performance can be achieved by using mixed alkyl chain lengths within the dialkyl quat.

The present invention relates to a foaming hair conditioner which comprises a monoalkyl quat from C14 to higher carbon chain lengths (preferably C16 to C22) and a mixture of dialkyl quats. In one dialkyl quat each alkyl is the same and is C16 and in the other each alkyl is the same and is C18. Also included is a propellant. Also optionally included is a silicone compound such as an amodimethicone, dimethicone, or dimethiconol.

The following is a description of ingredients which can be included in compositions of the invention.

Monoalkyl Quats

Monoalkyl quats can be compounds of the formula $N^+R^1R^2R^3R^4X^-$ wherein $R^1$, $R^2$, and $R^3$ are C1–C3 alkyl groups and $R^4$ is a C14 or greater alkyl group (preferably C16 to C22); and $X^-$ is any acceptable counterion such as chloride, bromide, methosulfate, ethosulfate, nitrate, acetate, phosphate or tosylate.

Non-limiting examples of monoalkyl quats are:

cetyltrimethylammonium chloride (C16);
stearyltrimethylammonium chloride (C18);
behenetrimethylammonium chloride (C22);
cetyltrimethyl ammonium bromide (C16);
soytrimonium chloride (C18);
tallowtrimonium chloride (C16/C18);
behentrimethylammonium methosulfate (C22);
Peg-2 Olealmonium chloride (C18);
palmityltrimethylammonium chloride (C16);
hydrogenated tallowtrimethylammonium chloride (C16/C18);
hydrogenated tallowtrimethylammonium bromide (C16/C18);
hydrogenated tallowtrimethylammonium methosulfate (C16/C18);
cetrimonium tosylate (C16): and
eicosyltrimethylammonium chloride (C20).

In compositions of the invention, said monoalkyl quat may be selected from the group consisting of behentrimonium chloride and cetrimonium chloride, most preferably, cetrimonium chloride.

Monoalkyl quats may be present in the composition from about 0.001 to 20% by weight, preferably from about 0.01 to 10% by weight, more preferably from 0.1 to 5% by weight, most preferably from about 0.45% to 1% by weight.

Dialkyl Quats

Dialkyl quats can be compounds of the formula $N^+R^5R^6R^7R^8X^-$ wherein $R^5$ and $R^6$ are C1–C3 alkyl groups and $R^7$ and $R^8$ are the same and each contains 16 carbon atoms; or $R^7$ and $R^8$ are the same and each contains 18 carbon atoms; and $X^-$ is any acceptable counterion such as chloride, bromide, methosulfate, ethosulfate, nitrate, acetate, phosphate; or tosylate.

Non-limiting examples of dialkyl quats are:
dicetyldimethylammonium chloride(C16);
distearyidimethylammonium chloride (C18);
dipalmityldimethylammonium chloride (C16);
dihyrogenatedtallowdimethylammonium chloride (C16/C18);
ditallowdimethylammonium chloride (C16/C18)
dihyrogenatedtallowdimethylammonium bromide (C16/C18)
dihyrogenatedtallowdimethylammonium methosulfate (C16/C18)

A mixture of dialkyl quats may be used in compositions of the invention.

The dialkyl quat in compositions of the invention is a mixture of C16, C16 dialkyl quat and C18, C18 dialkyl quat. The quats can be selected from the group consisting of dicetyldimonium chloride and distearyldimonium chloride.

An important aspect of the invention is the use of a mixture of alkyl chain lengths within the dialkyl quat to achieve superior conditioning performance.

The dialkyl quats within the dialkyl quat mixture, that is C16, C16 dialkyl quat and C18, C18 dialkyl quat, are present in a weight ratio of about 1:5 to about 5:1, preferably 1:4 to about 4:1, and most preferably 1:3 to about 3:1 and most preferably from about 1:2 to about 2:1. The C16 C16 dialkyl quat and C18 C18 dialkyl quat mixture may also have weight ratios of about 1:3 to about 2:1; 1:3 to about 1:1; 3:1 to about 2:1; 3:1 to about 1:1; and about 1:1.

Dialkyl quats may be present in the composition from about 0.001 to 20% by weight, preferably from about 0.01 to 10% by weight, more preferably from 0.1 to 5% by weight, most preferably from about 0.18% to 0.4% by weight.

The ratio of the monalkyl quat to dialkyl quat mixture in compositions of the invention is about 15:1 to about 2:1 or 1:1. The ratio of monalkyl quat to dialkyl quat in compositions of the invention may also be about 10:1 to about 2:1 or 1:1. The ratio of monalkyl quat to dialkyl quat in compositions of the invention may also be about 4:1 to about 2:1 or 1:1.

Silicone Compounds

Silicone compounds may optionally be used in compositions of the invention. A silicone compound may be selected from the group consisting of amodimethicone, dimethicone and dimethiconol.

Non-limiting examples of silicone compounds are:

DC929;
Octamethylcyclotetrasiloxane (D4),
DC 2-1784,
DC 1786,
DC 2-1780,
DC 2-949
DC 2-1784 and
Decamethylcyclopentasiloxane (D5).

Propellant

Packaged hair treatment compositions of the invention may contain an aerosol propellant. This agent is responsible for expelling the other materials from the container, and forming the mousse character.

The propellant gas can be any liquefiable gas conventionally used for aerosol containers. Examples of suitable propellants include dimethyl ether, propane, n-butane and isobutane, and hydrofluorocarbons such as propellant 152A, propellant 17A, used singly or admixed. Other examples of suitable propellants include nitrogen, carbon dioxide and compressed air.

The amount of the propellant gases is governed by normal factors well known in the aerosol art. For mousses the level of propellant is generally from about 2 to about 15%, optimally from about 4 to about 6% for a creamy foam and good sensory feel.

Optional ingredients which may be included in the compositions of the invention are hydrocarbons such as paraffin, vaseline solid paraffin, squalene, oligomer olefins and the like; amidoamines such as stearamidopropyl dimethylamine, isostearamidoethyl morpholine, behenamidopropyl dimethylamine and the like; humectants such as glycerine, propylene glycol, glycerol, sorbitol and the like; esters, such as isopropyl palmitate, isopropyl myristate, and stearyl stearate and the like; emulsifiers such as glyceryl monostearate, sorbitan monopalmitate, polyoxyethylene stearate and the like; cellulose derivatives such as hydroxypropylcellulose; cationic cellulose, hydroxyethyl cellulose and the like; thickening agents such as natural polymers and the like; and other ingredients such as solvents, bacteriocides, colors, and fragrances.

Compositions of the invention may be prepared by methods which are known to those skilled in the art. Ingredients used in the preparation of compositions of the invention are either known or may be prepared by known methods.

Compositions of the invention are used to condition hair by first wetting the hair, applying the composition of the invention as a mousse, working the mousse into the hair, and then rinsing the hair. Alternatively, water and a conditioner of the invention may be applied to the hair simultaneously. Alternately, a conditioner of the invention may be applied first, and then water. Conditioning with compositions of the invention may be done right after shampooing when the hair is still wet. Alternatively, conditioning the hair with compositions of the invention may be done separately from shampooing.

Compositions of the invention provide unexpectedly superior conditioning benefits when compared with prior art formulations. Compositions of the invention unexpectedly provide a consumer acceptable creamy foam using relatively low levels of monoalkyl quat, dialkyl quat, and silicone compounds.

Finally, compositions of the invention provide unexpectedly superior conditioning and styling attributes.

To demonstrate the new and unexpected results achieved by the present invention, the following compositions were prepared. These compositions illustrate the invention and do not limit the invention. These compositions are shown in the tables below.

EXAMPLES

Compositions of the present invention form creamy and excellent foams that in in-homes consumer test usage outperform conventional conditioning liquids of the same compositions. The table below details such formulations. These formulations may be made by methods which are known in the art or which are analogous to methods which are known in the art.

| Preferred Formula (Based on 100% Active Material) Description | Example Concentrate Wt % | Concentrate Ranges Wt % | Example Product Wt % |
|---|---|---|---|
| Water, Soft | 94.61 | | 90.83 |
| Cetrimonium Chloride* | 0.75 | 0.45–1% | 0.72 |
| Quaternium 18* | 0.30 | 0.18–0.4% | 0.29 |
| Cetyl/Stearyl Alcohol | 3.00 | 1.8–3.6% | 2.88 |
| Salt | 0.25 | 0–0.25% | 0.24 |
| Disodium EDTA | 0.10 | | 0.10 |
| Preservative | 0.15 | | 0.14 |
| Fragrance | 0.60 | | 0.58 |
| Silicone, DC 1786 | 0.24 | 0–0.5% | 0.23 |
| Propellant A50/DME (60:40 ratio) | | 3–6% (in product) | 4.00 |
| Total | 100.00 | | 100.00 |

The above formulas were made as follows:

1. Water phase is heated to 170° F.;
2. Cetrimonium Chloride, Quaternium-18 and Cetyl/Stearyl alcohol are added to the water phase under constant high-speed mixing;
3. The temperature of the mixture is maintained between 160–180° F. for about 40 minutes to ensure proper emulsification;
4. The salt solution is added below 160° F.;
5. Preservatives, fragrance, silicone agents are added below 110° F.;

6. The product is aerosolized using propellant as specified in the formula.

From the foregoing, it will be appreciated that although specific embodiments of the invention have been described herein for purposes of illustration, various modifications may be made without deviating from the spirit or scope of the invention.

What is claimed is:

1. A foaming and hair conditioning composition comprising:
   (a) a monoalkyl quat having 14 or greater carbon atoms in an alkyl substituent;
   (b) a dialkyl quat which is a mixture of a C16,C16 dialkyl quat and C18, C18 dialkyl quat;
   (c) a propellant; and
   (d) optionally a silicone.

2. A composition according to claim 1 wherein C16,C16 dialkyl quat and C18, C18 dialkyl quat are present in a weight ratio of about 1:3 to about 3:1.

3. A composition according to claim 1 wherein C16,C16 dialkyl quat and C18, C18 dialkyl quat are present in a weight ratio of about 1:2 to about 2:1.

4. A composition according to claim 1 wherein C16,C16 dialkyl quat and C18, C18 dialkyl quat are present in a weight ratio of about 1:3 to about 2:1.

5. A composition according to claim 1 wherein C16,C16 dialkyl quat and C18, C18 dialkyl quat are present in a weight ratio of about 1:3 to about 1:1.

6. A composition according to claim 1 wherein C16,C16 dialkyl quat and C18, C18 dialkyl quat are present in a weight ratio of about 3:1 to about 2:1.

7. A composition according to claim 1 wherein C16,C16 dialkyl quat and C18, C18 dialkyl quat are present in a weight ratio of about 3:1 to about 1:1.

8. A composition according to claim 1 wherein C16,C16 dialkyl quat and C18, C18 dialkyl quat are present in a weight ratio of about 1:5:1.

9. A composition according to claim 1 wherein the ratio of (a) to (b) is about 15:1 to about 2:1.

10. A composition according to claim 1 wherein the ratio of (a) to (b) is about 10:1 to about 2:1.

11. A composition according to claim 1 wherein the ratio of (a) to (b) is about 4:1 to about 2:1.

12. A composition in accordance with claim 1 wherein said monoalkyl quat is selected from the group consisting of behentrimonium chloride and cetrimonium chloride.

13. A composition in accordance with claim 1 wherein said dialkyl quat is a mixture of dicetyldimonium chloride and distearyldimonium chloride.

14. A composition in accordance with claim 1 wherein said monoalkyl quat is cetrimonium chloride.

15. A composition in accordance with claim 1 wherein said dialkyl quat is distearyldimonium chloride.

16. A composition in accordance with claim 1 wherein said propellant is selected from the group consisting of dimethyl ether, propane, n-butane, isobutane, nitrogen, carbon dioxide, compressed air, and mixtures thereof.

17. A composition in accordance with claim 1 wherein said propellant ranges in amount from about 3 to about 6% and consists of hydrocarbon.

18. A composition in accordance with claim 1 wherein said propellant ranges in amount from about 3 to about 6% and consists of hydrocarbon/DME in a ratio of about 60:40.

19. A method for conditioning hair which comprises contacting hair with a composition of claim 1.

* * * * *